US009636393B2

(12) United States Patent
Giuliani et al.

(10) Patent No.: US 9,636,393 B2
(45) Date of Patent: May 2, 2017

(54) COMPOSITIONS COMPRISING *NEISSERIA MENINGITIDIS* ANTIGENS FROM SEROGROUPS B AND C

(75) Inventors: Marzia Monica Giuliani, Siena (IT); Mariagrazia Pizza, Siena (IT); Rino Rappuoli, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 3603 days.

(21) Appl. No.: 10/148,533

(22) PCT Filed: Nov. 29, 2000

(86) PCT No.: PCT/IB00/01940
§ 371 (c)(1),
(2), (4) Date: Mar. 10, 2003

(87) PCT Pub. No.: WO01/37863
PCT Pub. Date: May 31, 2001

(65) Prior Publication Data
US 2005/0074450 A1    Apr. 7, 2005

(30) Foreign Application Priority Data
Nov. 29, 1999 (GB) .................................. 9928196.6

(51) Int. Cl.
A61K 39/095    (2006.01)
A61K 39/00     (2006.01)
A61K 39/42     (2006.01)
A61K 47/48     (2006.01)
A61K 39/116    (2006.01)

(52) U.S. Cl.
CPC .......... *A61K 39/095* (2013.01); *A61K 39/116* (2013.01); *A61K 47/4833* (2013.01); *A61K 47/48261* (2013.01); *A61K 2039/55505* (2013.01); *A61K 2039/55566* (2013.01); *A61K 2039/6037* (2013.01); *A61K 2039/6068* (2013.01)

(58) Field of Classification Search
None
See application file for complete search history.

(56) References Cited

U.S. PATENT DOCUMENTS

| | | | |
|---|---|---|---|
| 4,673,574 A | 6/1987 | Anderson | |
| 4,707,543 A * | 11/1987 | Zollinger et al. | 530/402 |
| 5,153,312 A | 10/1992 | Porro et al. | |
| 5,547,670 A | 8/1996 | Goldstein et al. | |
| 6,013,267 A | 1/2000 | Blake et al. | |
| 6,028,049 A | 2/2000 | Jacobs et al. | |
| 6,180,111 B1 | 1/2001 | Stein et al. | |
| 6,197,312 B1 | 3/2001 | Peak et al. | |
| 6,355,253 B1 | 3/2002 | Zlotnick | |
| 6,413,520 B1 | 7/2002 | Granoff | |
| 6,451,317 B1 | 9/2002 | Blake et al. | |
| 6,558,677 B2 | 5/2003 | Zollinger et al. | |
| 6,709,660 B1 | 3/2004 | Scarlato et al. | |
| 6,914,131 B1 | 7/2005 | Scarlato et al. | |
| 6,936,261 B2 | 8/2005 | Granoff et al. | |
| 7,018,636 B1 | 3/2006 | Bhattacharjee et al. | |
| 7,118,757 B1 | 10/2006 | Seid, Jr. et al. | |
| 7,348,006 B2 | 3/2008 | Contorni et al. | |
| 7,368,261 B1 | 5/2008 | Rappuoli | |
| 7,384,645 B2 | 6/2008 | Foster et al. | |
| 7,576,176 B1 * | 8/2009 | Fraser et al. | 530/350 |
| 7,604,810 B2 | 10/2009 | Rappuoli | |
| 7,628,995 B2 | 12/2009 | Bos et al. | |
| 7,731,967 B2 | 6/2010 | O'Hagan et al. | |
| 7,754,218 B2 | 7/2010 | Contorni et al. | |
| 7,838,014 B2 | 11/2010 | Biemans et al. | |
| 7,862,827 B2 | 1/2011 | Giuliani et al. | |
| 8,007,815 B1 | 8/2011 | Granoff et al. | |
| 8,029,807 B2 | 10/2011 | Bos et al. | |
| 8,114,960 B2 | 2/2012 | Arico et al. | |
| 8,663,656 B2 * | 3/2014 | Pizza | 424/249.1 |
| 8,703,914 B2 | 4/2014 | Arico et al. | |
| 8,808,711 B2 | 8/2014 | Oster et al. | |
| RE45,137 E | 9/2014 | O'Hagan et al. | |
| 8,968,748 B2 | 3/2015 | Granoff et al. | |
| 8,980,277 B2 | 3/2015 | Pizza | |
| 9,011,869 B2 | 4/2015 | Pizza | |
| 9,057,716 B2 | 6/2015 | Balocchi | |
| 9,139,621 B2 | 9/2015 | Fraser | |

(Continued)

FOREIGN PATENT DOCUMENTS

| | | |
|---|---|---|
| EP | 0011243 | 5/1980 |
| EP | 0273116 A2 | 7/1988 |
| EP | 0467714 A1 | 1/1992 |
| EP | 1741443 B1 | 10/2007 |
| EP | 1790660 B1 | 6/2012 |
| WO | WO-90/06696 A2 | 6/1990 |
| WO | WO-9006696 | 6/1990 |
| WO | WO-92/16643 A1 | 10/1992 |
| WO | WO 95/03413 A1 | 2/1995 |
| WO | WO-95/33049 A2 | 12/1995 |
| WO | WO 96/29412 A1 | 9/1996 |

(Continued)

OTHER PUBLICATIONS

Colman PM. Research Immunol. 145: 33-36, 1994.*
McGuinnes et al. Mol. Microbiol. 7: 505-514, Feb. 1993.*
McGuinnes et al. Lancet 337: 514-517, Mar. 1991.*
Skolnick et al. Trends in Biotechnology 18: 34-39, 2000.*
Greenspan et al. Nature Biotechnology 17: 936-937, 1999.*
Bjune et al., "Effect of outer membrane vesicle vaccine against group B meningococcal disease in Norway," Lancet 338(8775):1093-1096, 1991.

(Continued)

*Primary Examiner* — S. Devi
(74) *Attorney, Agent, or Firm* — Morrison & Foerster LLP

(57) ABSTRACT

International patent application WO99/61053 discloses immunogenic compositions that comprise *N. meningitidis* serogroup C oligosaccharide conjugated to a carrier, in combination with *N. meningitidis* serogroup B outer membrane protein. These are disclosed in the present application in combination with further Neisserial proteins and/or protective antigens against other pathogenic organisms (e.g. *Haemophilus influenzae*, DTP, HBV, etc.).

7 Claims, 2 Drawing Sheets

(56) References Cited

U.S. PATENT DOCUMENTS

| | | | |
|---|---|---|---|
| 9,150,898 B2 | 10/2015 | Arico | |
| 9,156,894 B2 | 10/2015 | Masignani et al. | |
| 2002/0160016 A1 | 10/2002 | Peak et al. | |
| 2003/0068336 A1 | 4/2003 | Ryall | |
| 2004/0092711 A1 | 5/2004 | Arico | |
| 2004/0110670 A1 | 6/2004 | Arico et al. | |
| 2006/0029621 A1 | 2/2006 | Granoff et al. | |
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2007/0059329 A1 | 3/2007 | Norals et al. | |
| 2007/0082014 A1 | 4/2007 | Costantino | |
| 2008/0241180 A1 | 10/2008 | Contorni | |
| 2009/0232820 A1 | 9/2009 | Fraser et al. | |
| 2010/0267931 A1 | 10/2010 | Arico et al. | |
| 2011/0182942 A1 | 7/2011 | Zollinger | |
| 2011/0262484 A1 | 10/2011 | Feavers | |
| 2013/0236489 A1 | 9/2013 | Serruto et al. | |

FOREIGN PATENT DOCUMENTS

| | | |
|---|---|---|
| WO | WO-97/13860 A1 | 4/1997 |
| WO | WO 97/28273 A1 | 8/1997 |
| WO | WO-9858670 | 12/1998 |
| WO | WO 99/24578 A2 | 5/1999 |
| WO | WO 99/31132 A1 | 6/1999 |
| WO | WO-99/33488 | 7/1999 |
| WO | WO 99/36544 A2 | 7/1999 |
| WO | WO 99/55873 A2 | 11/1999 |
| WO | WO 99/57280 A2 | 11/1999 |
| WO | WO 99/58683 A2 | 11/1999 |
| WO | WO 99/61053 A1 | 12/1999 |
| WO | WO-00/22430 A2 | 4/2000 |
| WO | WO-00/66741 A2 | 11/2000 |
| WO | WO 00/66791 A1 | 11/2000 |
| WO | WO-00/66791 A1 | 11/2000 |
| WO | WO-00/71725 A2 | 11/2000 |
| WO | WO-01/31019 A2 | 5/2001 |
| WO | WO-01/34642 | 5/2001 |
| WO | WO-01/52885 A1 | 7/2001 |
| WO | WO-01/64920 A2 | 9/2001 |
| WO | WO-01/64922 A2 | 9/2001 |
| WO | WO-01/91788 A1 | 12/2001 |
| WO | WO-02/09643 | 2/2002 |
| WO | WO-02/058737 A2 | 8/2002 |
| WO | WO-02/080965 A2 | 10/2002 |
| WO | WO-03/007985 A2 | 1/2003 |
| WO | WO-03/009869 A1 | 2/2003 |
| WO | WO-03/010194 A2 | 2/2003 |
| WO | WO-03/020756 A2 | 3/2003 |
| WO | WO-03/094834 A2 | 11/2003 |
| WO | WO-2004/019977 | 3/2004 |
| WO | WO-2004/032958 A1 | 4/2004 |
| WO | WO-2004/048404 A2 | 6/2004 |
| WO | WO-2004/054611 A1 | 7/2004 |
| WO | WO-2004/103400 A2 | 12/2004 |
| WO | WO-2005/004908 | 1/2005 |
| WO | WO-2005/064021 A2 | 7/2005 |
| WO | WO-2005/106009 A2 | 11/2005 |
| WO | WO-2006/046143 A2 | 5/2006 |
| WO | WO-2009/158142 A1 | 12/2009 |

OTHER PUBLICATIONS

Claassen et al., "Production, characterization and control of a Neisseria meningitidis hexavalent class 1 outer membrane protein containing vesicle vaccine," Vaccine 14(10):1001-1008, 1996.
Corbel, "Control testing of combined vaccines: a consideration of potential problems and approaches," Biologicals 22(4):353-360, 1994.
Manning et al., "OMP85 Proteins of Neisseria gonorrhoeae and Neisseria meningitidis are similar to Haemophilus influenzae D-15-AG and Pasteurella multocida OMA87," Microbial Pathogenesis 25(1):11-21, 1998.
Nassif et al., "Roles of pilin and PilC in adhesion of Neisseria meningitidis to human epithelial and endothelial cells," Proc. Natl. Aca. Sci. USA 91(9):3769-3773, 1994.
Parkhill et al., "Complete DNA sequence of a serogoup A strain of Neisseria meningitidis Z2491," Nature 404:502-506, 2000.
Peeters et al., "Phase I clinical trial with a hexavalent PorA containing meningococcal outer membrane vesicle vaccine," Vaccine 14(10):1009-1015, 1996.
Peltola, "Prophylaxis of bacterial meningitis," Infectious Disease Clinics of North America 13(3):685-710, 1999.
Romero et al., "Current status of Meningococcal group B vaccine candidates: capsular or noncapsular?" Clin. Microbiol. Rev. 7(4):559-575, 1994.
Schuchat et al., "Bacterial meningitis in the United States in 1995," N. Engl. J. Med. 337(14):970-976, 1997.
Tettelin et al., "Complete genome sequence of Neisseria meningitidis serogroup B strain MC58," Science 287:1809-1815, 2000.
Van Der Ley et al., "Construction of Neisseria meningitidis strains carrying multiple chromosomal copies of the porA gene for use in the production of a multivalent outer membrane vesicle vaccine," Vaccine 13(4):401-407, 1995.
Fredriksen at al. (1991). "Production, characterization and control of MenB-vaccine "Folkehelsa": an outer membrane vesicle vaccine against group B meningococcal disease," NIPH Annals 14:67-79.
Koeberling et al. (2007). "Improved immunogenicity of a H44/76 group B outer membrane vesicle vaccine with over-expressed genome-derived Neisserial antigen 1870," Vaccine 25:1912-1920.
"VA-MENGOC-BC," Product information from S.C.S. Farmacia Manes, Argentina. 1 page.
Constantino et al. (1992). "Development and phase 1 clinical testing of a conjugate vaccine against meningococcus A and C," Vaccine, 10(10), 691-698.
Granoff et al. (May 1997). "MF59 Adjuvant Enhances Antibody Responses of Infant Baboons Immunized with Haemophilus Influenza Type b and Neisseria meningitides Group C Oligosaccharide-CRM197 Conjugate Vaccine," Infection and Immunity, 65(5):1710-1715.
Lieberman et al. (May 15, 1996). "Safety and Immunogenicity of a Serogroups A/C Neisseria meningitidis Oligosaccharide-Protein conjugate Vaccine in Young Children", JAMA, 275(19):1499-1503.
Rosenqvist et al. (1998). "Effect of Aluminum Hydroxide and Meningococcal Serogroup C Capsular Polysaccharide on the Immunogenicity and Reactogenicity of a Group B Neisseria meningitidis Outer Membrane Vesicle Vaccine," Developments in Biological Standardization, vol. 92, pp. 323-333.
International Preliminary Examination Report mailed Aug. 23, 2000, for international patent application No. PCT/US99/11977, filed May 28, 1999.
Katial et al. (2002). "Immunogenicity and Safety Testing of a Group B Intransal Meningococcal Native Outer Membrane Vesicle Vaccine," Infection and Immunity 70(2):702-707.
Arigita, C. at al. "Stability of mono- and trivalent meningococcal outer membrane vesicle vaccines," Vaccine, vol. 22, No. 5-0, 2004, pp. 630-643.
Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.
Centers for Disease Control and Prevention (2012). "Child & Adolescent Past Immunization Schedules—Consolidated Historical Records," Excerpts from website, 7 pages.
Centers for Disease Control and Prevention (Jan. 18, 2002) "Notice to readers: Recommended childhood immunization schedule—United States, 2002," MMWR Weekly 51(02):31-3.
Centers for Disease Control and Prevention (Jan. 21, 2000) "Notice to readers: Recommended childhood immunization schedule—United States, 2000," MMWR Weekly 49(02):35-8,47.

(56) References Cited

OTHER PUBLICATIONS

Chippaux et al. (Sep. 3, 2004). "Immunogenicity, safety, and memory of different schedules of Neisseria meningitidis A/C-diphtheria toxoid conjugate vaccine in infants in Niger," Vaccine 22(25-26):3303-11.
Dalseg et al. (May 14, 1999). "Outer membrane vesicles from group B meningococci are strongly immunogenic when given intranasally to mice" Vaccine 17(19):2336-2345.
De Kleijn, Ed. et al. "Immunogenicity and safety of a hexavalent meningococcal outer membrane-vesicle vaccine in children of 2-3 and 7-8 years of age," Vaccine, 18:1456-1466(2000).
De Moraes JC, et al. (1992). Protective efficacy of a serogroup B meningococcal vaccine in Sao Paulo, Brazil. Lancet 340: 1074-1078.
Deacon et al. (1982) "A comparative clinical study of Adsorbed Tetanus Vaccine and Adult-type Tetanus-Diphtheria Vaccine," J Hyg Camb 89: 513-519.
Debbag et al., "Evaluation of Adverse Reactions Associated to Antimeningococcal BC Vaccination in 16,700 Children" Clinical Infectious Diseases, vol. 21, pp. 790-A420 (Sep. 1995).
Decision revoking EP1644035, filed in Opposition against EP1644035, dated Jan. 20, 2014, 14 pages.
Declaration from Christiane Feron, filed in opposition against EP1534326, dated Sep. 28, 2009, 3 pages.
Devoe et al. (1973). "Release of endotoxin in the form of cell wall blebs during in vitro growth of Neisseria meningitidis," J Exp Med, 138(5):1156-67.
EMEA (May 4, 2010) "CHMP Assessment Report for Menveo™," 58 pages.
Experimental data regarding OMV expression following OMV extraction, filed in opposition against EP1534326, dated Oct. 2, 2009, 1 page.
Experimental data: expression of NspA, '287' and '741' on 3 strains of bacteria, filed in opposition against EP1534326, dated Aug. 4, 2010. 2 pages.
Frasch et al. (2001). "Outer Membrane Protein Vesicle Vaccines for Meningococcal Disease," Chapter 7 in "Methods in Molecular Medicine, Meningococcal Vaccines: Methods and Protocols," Pollard et al. (Ed), Humana Press, Totowa, New Jersey, vol. 66, pp. 81-107.
Fukasawa et al. (1999) "Neisseria meningitidis serogroup C polysaccharide and serogroup B outer membrane vesicle conjugate as a bivalent meningococcus vaccine candidate." Vaccine 17:2951-2958.
Fukasawa et al. (2004). "Adjuvant can improve protection induced by OMV vaccine against Neisseria meningitidis serogroups B/C in neonatal mice" FEMS Immunol. Med. Microbiol. 41:205-210.
Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).
Granoff, D. and Harris, S. (2004) "Protective Activity of Group C Anticapsular Antibodies Elicited in Two-year-olds by an Investigational Quadrivalent Neisseria Meningitidis-Diphtheria Toxoid Conjugate Vaccine," The Pediatric Infectious Disease Journal 23(6):490-497.
Henry, et al. (2004). "Improved methods for producing outer membrane vesicles in Gram-negative bacteria," Research in Microbiology, 155:437-446.
Hoiby et al. (1991). "Bactericidal antibodies after vaccination with the Norwegian meningococcal serogroup B outer membrane vesicle vaccine: a brief survey," NIPH Annals 14(2):147-155.
Hoiby et al. (1991). "The Norwegian meningococcal serogroup B outer membrane vesicle vaccine protection trials: case tracing, meningococcal antigen detection and serological diagnosis," NIPH Annals, 14(2):107-123.
Holst et al. (2003). "Serum bactericidal activity correlates with the vaccine efficacy of outer membrane vesicle vaccines against Neisseria meningitidis serogroup B disease," Vaccine 21(7-8):734-737.
Interlocutory decision in opposition proceedings, filed in opposition against EP1534326, dated Mar. 25, 2010, 11 pages.
List of Journals from SpringerProtocols website about Methods in Molecular Biology, filed in Opposition against EP1644035, dated Oct. 18, 2014, 5 pages.
McVernon et al. (2003) "Effect of infant immunisation with meningococcus serogroup C-CRM(197) conjugate vaccine on diphtheria immunity and reactogenicity in pre-school aged children," Vaccine 21(19-20):2573-2579.
Milagres et al. (2000) "Bactericidal antibody response to Neisseria meningitidis serogroup B in patients with bacterial meningitis: effect of immunization with an outer membrane protein vaccine," FEMS Immunology and Medical Microbiology 28(4):319-327.
Norheim et al. (2004). "Immunogenicity and bactericidal activity in mice of an outer membrane protein vesicle vaccine against Neisseria meningitidis serogroup A disease," Vaccine, 22: 2171-2180.
Norheim et al. (2005). "Development and characterisation of outer membrane vesicle vaccines against serogroup A Neisseria meningitidis" Vaccine 23(29):3762-3774.
Notice of Appeal by Carpmaels & Ransford, filed in Opposition against EP1644035, dated Mar. 24, 2014, 1 page.
Notice of Appeal by GlaxoSmithKline Biologicals S.A., filed in relation to EP1534326, dated Jun. 3, 2010, 2 pages.
Notice of opposition by GlaxoSmithKline Biologicals S.A., filed in opposition against EP1534326, dated Mar. 3, 2008, 19 pages.
Notice of Opposition, filed in Opposition against EP1644035, dated May 24, 2012, 15 pages.
O'Hallahan J, et al. 2004. The strategy to control New Zealand's epidemic of Group B meningococcal disease. PIDJ 23: S293-S298.
Oster et al. (2007). "Immunogenicity and safety of a strain-specific MenB OMV vaccine delivered to under 5-year olds in New Zealand," Vaccine, 25:3075-9.
Patentee's response to Notice of Opposition, filed in Opposition against EP1644035, dated Mar. 12, 2013, 9 pages.
Patentee's response to opposition, filed in opposition against EP1534326, dated Jan. 19, 2009, 11 pages.
Perkins et al. (1998). "Immunogenicity of two efficacious outer membrane protein-based serogroup B meningococcal vaccines among young adults in Iceland," *The Journal of Infectious Disease* 177:683-691.
Pichichero et al. (Jan. 2005) "Comparative trial of the safety and immunogenicity of quadrivalent (A, C, Y, W-135) meningococcal polysaccharide-diphtheria conjugate vaccine versus quadrivalent polysaccharide vaccine in two- to ten-year-old children," Pediatr Infect Dis J. 24(1):57-62.
Pillai et al. (2005) "Outer membrane protein (OMP) based vaccine for Neisseria meningitidis serogroup B," Vaccine 23(17-18):2206-2209.
Poolman et al. "Comparison of Meningococcal Outer Membrane Protein Vaccines Solubilized with Detergent or C Polysaccharide," Antonie van Leeuwenhoek, 53:413-419 (1987).
Ramsay et al. (2001) "Efficacy of meningococcal serogroup C conjugate vaccine in teenagers and toddlers in England" Lancet 357(9251):195-196.
Rennels et al. (May 2004) "Dosage escalation, safety and immunogenicity study of four dosages of a tetravalent meningococcal polysaccharide diphtheria toxoid conjugate vaccine in infants," The Pediatric Infectious Disease Journal 23(5):429-435.
Rennels et al. (Oct. 2002) "Dose escalation, safety and immunogenicity study of a tetravalent meningococcal polysaccharide diphtheria conjugate vaccine in toddlers," The Pediatric Infectious Disease Journal 21(10):978-979.
Reply to Statement of Grounds of Appeal by Nederlandsch Octrooibureau, filed in Opposition against EP1644035, dated Oct. 15, 2014, 8 pages.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Sierra et al. (1991). "Vaccine against group B Neisseria meningitidis: protection trial and mass vaccination results in Cuba," NIPH Ann 14: 195-207.

(56) References Cited

OTHER PUBLICATIONS

Slide printout by Carpmaels & Ransford, filed in opposition against EP1534326, dated Nov. 23, 2009, 2 pages.
Statement of Grounds of Appeal by Carpmaels & Ransford, filed in Opposition against EP1644035, dated May 30, 2014, 5 pages.
Statement of Grounds of Appeal by GlaxoSmithKline Biologicals S.A., filed in relation to EP1534326, dated Aug. 4, 2010, 24 pages.
Van de Waterbeemd (2012). "Identification and optimization of critical process parameters for the production of NOMV vaccine against Neisseria meningitidis," Vaccine, 30(24):3683-90.
Van der Ley & Steeghs (2003) "Lessons from an LPS-deficient Neisseria meningitidis mutant" Journal of Endotoxin Research 9(2):124-128.
Van der Ley et al. (1992). "Construction of a Multivalent Meningococcal Vaccine Strain Based on the Class I Outer Membrane Protein," *Infection and Immunity* 60(8): 3516-3161.
Verheul et al., (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.
Wedege et al. (2003). "Antibody specificities and effect of meningococcal carriage in Icelandic teenagers receiving the Norwegian serogroup B outer membrane vesicle vaccine," Infect. Immun. 71:3775-3781.
Williams et al., (2007) "Proteomic analysis of outer membranes and vesicles from wild-type serogroup B Neisseria meningitidis and a lipopolysaccharide-deficient mutant" Infection and Immunity 75(3):1364-1372.
Wilson & Walker (Eds.) (1994). "Wilson Principles and techniques of practical biochemistry: Editors: Bryan L. Williams and Keith Wilson," Cambridge University Press, Cambridge, fourth edition, pp. 309.
World Health Organization official document. 1999. Standardization and validation of serological assays for the evaluation of immune responses to Neisseria meningitidis serogroup A/C vaccines. Mar. 8-9, 1999.
Written submission in preparation to oral proceedings by Carpmaels & Ransford, filed in Opposition against EP1644035, dated Oct. 18, 2013, 2 pages.
Written submission in preparation to oral proceedings by GlaxoSmithKline Biologicals S.A., filed in opposition against EP1534326, dated Sep. 30, 2009, 24 pages.
Written submission in preparation to oral proceedings by Nederlandsch Octrooibureau, filed in Opposition against EP1644035, dated Oct. 18, 2013, 6 pages.
Zollinger et al. (2010). "Design and evaluation in mice of a broadly protective meningococcal group B native outer membrane vesicle vaccine," Vaccine, 28(31):5057-5067.
Artenstein, M.S. (1975). "Control of Meningococcal Meningitis with Meningococcal Vaccines." Yale J. Biol. Med. 48(3):197-200.
Boslego et al. (1991). "Gonorrhea Vaccines," Chapter 17 *In Vaccines and Immunotherapy*, Cryz S.J. (Ed.), Pergamon Press: New York, NY, pp. 211-223.
CECMED (Dec. 2, 2011), "Resumen de las Caracteristicas del Producto: VA-MENGOC-BC," Ministerio de Salud Publica de Cuba, 4 pages. (3 page English translation included).
Collins (2011). "Gram-negative outer membrane vesicles in vaccine development," Discov Med, 12(62):7-15.
Cruse et al. (2003). Illustrated Dictionary of Immunology, $2^{nd}$ Ed. CRC Press, pp. 46, 166, and 382.
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Decision revoking EP1534326, filed in Opposition against EP1534326, dated Jan. 15, 2016, 3 pages.
Decision revoking EP1737486, filed in opposition against EP1737486, dated Oct. 28, 2015, 28 pages.

Donnelly et al. (2010). "Qualitative and quantitative assessment of meningococcal antigens to evaluate the potential strain coverage of protein-based vaccines," Proc Natl Acad Sci U S A, 107(45):19490-5.
Ellis et al. (2010). "Virulence and immunomodulatory roles of bacterial outer membrane vesicles," Microbiol Mol Biol Rev, 74(1):81-94.
Ferrari et al. (2006). "Outer membrane vesicles from group B Neisseria meningitidis delta gna33 mutant: proteomic and immunological comparison with detergent-derived outer membrane vesicles," Proteomics, 6(6):1856-66.
Galeano et al. (1995). "Efectividad de una vacuna antimeningococcica en una cohorte de itagui, Colombia, 1995," Epidemiologico de Antioquia 20(2), 8 pages. (9 page English translation included).
Gervais et al. (1992). "Putative Lipoprotein Yaec Precursor," Database Swissport Acc No. p28635.
Gil et al. (2009). "Proteomic study via a non-gel based approach of meningococcal outer membrane vesicle vaccine obtained from strain CU385," Human Vaccines 5(5):347-356.
Giuliani et al. (2010). "Measuring antigen-specific bactericidal responses to a multicomponent vaccine against serogroup B meningococcus," Vaccine 28:5023-5030.
Holst et al. (2009). "Properties and clinical performance of vaccines containing outer membrane vesicles from Neisseria meningitidis," Vaccine; 27 Suppl 2:B3-12.
Jacobsson et al. (2009). "Prevalence and sequence variations of the genes encoding the five antigens included in the novel 5CVMB vaccine covering group B meningococcal disease" Vaccine. 27:1579-1584.
Legrain et al. (1995). "Production of Lipidated Meningococcal Transferrin Binding Protein 2 in *Escherichia Coli*," *Protein Expression and Purification* 6:570-578.
Lucidarme et al., (2010). "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Martin et al. (1998). "New Zealand epidemic of meningococcal disease identified by a strain with phenotype B:4:P1.4," JID 177:497-500.
McLeod et al. (2000). "Structural relationships and sialylation among meningococcal L1, L8, and L3,7 lipooligosaccharide serotypes," J Biol Chem, 275(13):9716-24.
Morley, S. et al. (Dec. 12, 2001). "Vaccine prevention of meningococcal disease, coming soon?" *Vaccine* 20(5-6):666-687.
Novartis (Jun. 9, 2011). "Novartis candidate vaccine Bexsero® shows significant potential in providing broad coverage against meningococcal serogroup B infections." Media Release, 6 pages.
Novartis internal data, filed in relation to EP1902726, submitted on Apr. 13, 2015, 1 page.
Ochoa, Rolando (2008). "Main projects on research, development and manufacturing of human vaccines," excerpt from presentation at BioQatar Symposium 2008, 4 slides.
Perez et al. (2010). "Community acquired bacterial meningitis in Cuba: a follow up of a decade," BMC Infectious Diseases 10:130, 9 pages.
Pizza et al. (2000). "Identification of Vaccine Candidates Against Serogroup B Meningococcus by Whole-Genome Sequencing," Science 287(5459):1816-1820.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Poolman et al. (1986). "Class 1/3 outer membrane protein vaccine against group B, type 15, subtype 16 meningococci." Dev. Biol. Stand. Abstract only. 63:147-52.

(56) References Cited

OTHER PUBLICATIONS

Renauld-Mongenie et al. (1997). "Identification of Human Transferrin-Binding Sites Within Meningococcal Transferrin-Binding Protein B," *J. Bacteriology* 197(20):6400-6407.

Rodriguez et al. (1999). "The epidemiological impact of antimeningococal B vaccination in Cuba," Mem Inst Oswaldo Cruz 94(4):433-440.

Sacchi et al. (2001). "Serosubtypes and PorA types of Neisseria meningitidis serogroup B isolated in Brazil during 1997-1998: overview and implications for vaccine development," J Clin Microbiol, 39(8):2897-903.

Seib et al. (2010). "Influence of serogroup B meningococcal vaccine antigens on growth and survival of the meningococcus in vitro and in ex vivo and in vivo models of infection," Vaccine 28(12):2416-2427.

Serruto et al. (2010). "Neisseria meningitidis GNA2132, a heparin-binding protein that induces protective immunity in humans," PNAS 107(8):3770-3775.

Statement of grounds of appeal, filed in relation to EP1902726, dated Apr. 13, 2015, 9 pages.

Statement of Grounds of Appeal, filed in relation to EP2353608, dated Jul. 22, 2015, 8 pages.

Summons to Attend Oral Hearings dated May 3, 2016, for EP2275129, 8 pages.

Tavano et al. (Jul. 2000). "The membrane expression of Neisseria meningitidis adhesin A (NadA) increases the proimmune effects of MenB OMVs on human macrophages, compared with NadA-OMVs, without further stimulating their proinflammatory activity on circulating monocytes," J Leukoc Biol 86(1):143-153.

Tettelin et al. (Mar. 10, 2000). "Complete Genome Sequence of Neisseria meningitidis Serogroup B Strain MC58," Science 287(5459):1809-1815.

Vermont et al. (2003). "Meningococcal serogroup B infections: a search for a broadly protective vaccine," Expert Rev Vaccines, 2(5):673-81.

Voulhoux and Tommassen (2002). "Transport of lipoproteins to the cell surface in Neisseria meningitidis," 13th International Pathogenic Neisseria Conference 2002, p. 31.

Welsch et al. (2002). "Genome-derived antigen (GNA) 2132 elicits protective serum antibodies to groups B and C Neisseria meningitidis strains," 13th International Pathogenic Neisseria Conference 2002, p. 25.

Welsch et al. (2003). "Antibody to genome-derived neisserial antigen 2132, a Neisseria meningitidis candidate vaccine, confers protection against bacteremia in the absence of complement-mediated bactericidal activity" Journal of Infectious Diseases 188 (11):1730-1740.

* cited by examiner

COMPOSITIONS COMPRISING *NEISSERIA MENINGITIDIS* ANTIGENS FROM SEROGROUPS B AND C

This application is a §371 filing from PCT/IB00/01940, filed Nov. 29, 2000, which claims priority from GB 9928196.6, filed Nov. 29, 1999, from which applications priority is claimed pursuant to the provisions of 35 U.S.C. §§119/120.

All documents cited herein are hereby incorporated by reference in their entirety.

TECHNICAL FIELD

This invention is in the field of immunogenic compositions, more particularly those comprising combinations of immunogenic molecules from *Neisseria meningitidis* serogroups B and C (NmB and NmC).

BACKGROUND ART

Serogroup B and C strains of *Neisseria meningitidis* (Nm) together account for the majority of invasive diseases in Europe and the United States. Vaccines against individual Nm serogroups are presently available. The NmB vaccine from the Norwegian National Institute of Public Health is safe, elicits strain-specific immunity in children and adults, and is efficacious in preventing NmB disease in adolescents. This vaccine has typically been combined with meningococcal C polysaccharide vaccine and given with alum. The plain polysaccharide vaccine component, however, is not effective in infants and young children. The Chiron NmC conjugate (conj.) vaccine is also safe, elicits high titres of serum bactericidal antibody in infants vaccinated as young as two and three months of age, and induces immunologic B cell memory to the unconjugated NmC polysaccharide.

To provide a combination vaccine for NmB and NmC which induces an immune response to both serogroups, international patent application WO99/61053 discloses immunogenic compositions that comprise (a) NmC oligosaccharide conjugated to a carrier, in combination with (b) NmB outer membrane protein. The combination vaccine induces an immune response to both serogroups that is not significantly different from the immune response induced by each serogroup alone. It is an object of the present invention to develop these into compositions that induce immune responses against a wider variety of organisms.

DISCLOSURE OF THE INVENTION

Accordingly, the invention provides an immunogenic composition comprising (a) NmC oligosaccharide and (b) NmB outer membrane protein, characterised in that the composition also comprises (c) one or more of the following:
  the proteins disclosed in WO99/57280 or immunogenic fragments thereof;
  the proteins disclosed in WO99/36544 or immunogenic fragments thereof;
  the proteins disclosed in WO99/24578 or immunogenic fragments thereof;
  the proteins disclosed in WO97/28273 or immunogenic fragments thereof;
  the proteins disclosed in WO96/29412 or immunogenic fragments thereof;
  the proteins disclosed in WO95/03413 or immunogenic fragments thereof;
  the proteins disclosed in WO99/31132 or immunogenic fragments thereof;
  a protective antigen against *Neisseria meningitidis* serogroup A;
  a protective antigen against *Neisseria meningitidis* serogroup Y;
  a protective antigen against *Neisseria meningitidis* serogroup W;
  a protective antigen against *Haemophilus influenzae*;
  a protective antigen against *pneumococcus*;
  a protective antigen against diphtheria;
  a protective antigen against tetanus;
  a protective antigen against whooping cough;
  a protective antigen against *Helicobacter pylori*;
  a protective antigen against polio; and/or
  a protective antigen against hepatitis B virus.

As well as inducing an immune response to both *N. meningitidis* B and C, the immunogenic compositions of the invention can induce an immune response against further organisms.

Component (a)

The oligosaccharide of component (a) is preferably the Chiron oligosaccharide, representing NmC polysaccharide fragments of from preferably about 12 to about 22 repeating units.

The NmC oligosaccharide of component (a) is preferably conjugated to a carrier. The carrier is preferably a protein, but may alternatively be a polysaccharide, polylactic acid, polyglycolic acid, polymeric amino acids, amino acid co-polymer, lipid aggregate, or inactive virus particle.

More preferably, the carrier is a protein. Most preferably, the carrier is CRM197, a non-toxic diphtheria toxin. Each dose preferably has 10 µg of oligosaccharide to 12.5-33 µg CRM197 (i.e. to maintain a oligo/protein ratio of from about 0.3 to about 0.8). More preferably, about 20 µg of CRM197 can be used.

The dosage of NmC conjugate or polysaccharide is expressed in µg of sialic acid. An NmC vaccine containing unconjugated polysaccharide (referred to herein as "NmC polysaccharide" or "MenC Ps") can also be used. MenC Ps is a crude isolate comprising polysaccharides preferably from about 60 to about 80 repeating units.

For further details of NmC-CRM197 conjugation, see Costantino et al. (1992) *Vaccine* 10:691-698.

Component (b)

The NmB outer membrane protein of component (b) preferably comprises partially purified outer membrane proteins from strain 44/76 (B 15:P1.7, 16:L3,7,9).

The outer membrane protein is preferably present as proteoliposomic vesicles, obtained for example as a result of the extraction process using deoxycholate.

The dosage of NmB is expressed in µg of protein. Preferably, the NmB immune composition/vaccine components can be obtained from the National Institute of Public Health of Norway. The NmB/alum vaccine comprises 0.05 mg/ml NmB protein, 3.33 mg/ml Al(OH)$_3$ (alum), and 0.10 mg/ml thiomersalsodium.

Component (c)

Preferably, component (c) comprises one or more of:
  a protein comprising an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, & 892, as disclosed in WO99/24578 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs);

a protein comprising an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, & 90, as disclosed in WO99/36544 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs);

a protein comprising an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 5.12, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, 1828, 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, 2866, 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018 & 3020, as disclosed in WO99/57280 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs);

SEQ ID NO: 1200 of WO99/57280 is SEQ ID
NO: 1 herein:
MFKRSVIAMACIFPLSACGGGGGGSPDVKSADTPSKPAAPVVAENAGEGV

LPKEKKDEEAAGGAPQADTQDATAGEGSQDMAAVSAENTGNGGAATTDNP

-continued
KNEDAGAQNDMPQNAAESANQTGNNQPAGSSDSAPASNPAPANGGSDFGR

TNVGNSVVIDGPSQNITLTHCKGDSCNGDNLLDEEAPSKSEFEKLSDEEK

IKRYKKDEQRENFVGLVADRVKKDGTNKYIIFYTDKPPTRSARSRRSLPA

EIPLIPVNQADTLIVDGEAVSLTGHSGNIFAPEGNYRYLTYGAEKLPGGS

YALRVQGEPAKGEMLVGTAVYNGEVLHFHMENGRPYPSGGRFAAKVDFGS

KSVDGIIDSGDDLHMGTQKFKAAIDGNGFKGTWTENGGGDVSGRFYGPAG

EEVAGKYSYRPTDAEKGGFGVFAGKKDRD,

SEQ ID NO: 1202 of WO99/57280 is SEQ ID
NO: 2 herein:
MFKRSVIAMACIFALSACGGGGGGSPDVKSADTLSKPAAPVVSEKETEAK

EDAPQAGSQGQGAPSAQGSQDMAAVSEENTGNGGAVTADNPKNEDEVAQN

DMPQNAAGTDSSTPNHTPDPNMLAGNMENQATDAGESSQPANQPDMANAA

DGMQGDDPSAGGQNAGNTAAQGANQAGNNQAAGSSDPIPASNPAPANGGS

NFGRVDLANGVLIDGPSQNITLTHCKGDSCSGNNFLDEEVQLKSEFEKLS

DADKISNYKKDGKNDKFVGLVADSVQMKGINQYIIFYKPKPTSFARFRRS

ARSRRSLPAEMPLIPVNQADTLIVDGEAVSLTGHSGNIFAPEGNYRYLTY

GAEKLPGGSYALRVQGEPAKGEMLAGAAVYNGEVLHFHTENGRPYPTRGR

FAAKVDFGSKSVDGIIDSGDDLHMGTQKFKAAIDGNGFKGTWTENGSGDV

SGKFYGPAGEEVAGKYSYRPTDAEKGGFGVFAGKKEQD, and

SEQ ID NO: 1204 of WO99/57280 is SEQ ID
NO: 3 herein:
MFKRSVIAMACIVALSACGGGGGGSPDVKSADTLSKPAAPVVTEDVGEEV

LPKEKKDEEAVSGAPQADTQDATAGKGGQDMAAVSAENTGNGGAATTDNP

ENKDEGPQNDMPQNAADTDSSTPNHTPAPNMPTRDMGNQAPDAGESAQPA

NQPDMANAADGMQGDDPSAGENAGNTADQAANQAENNQVGGSQNPASSTN

PNATNGGSDFGRINVANGIKLDSGSENVTLTHCKDKVCDRDFLDEEAPPK

SEFEKLSDEEKINKYKKDEQRENFVGLVADRVEKNGTNKYVIIYKDKSAS

SSSARFRRSARSRRSLPAEMPLIPVNQADTLIVDGEAVSLTGHSGNIFAP

EGNYRYLTYGAEKLSGGSYALSVQGEPAKGEMLAGTAVYNGEVLHFHMEN

GRPSPSGGRFAAKVDFGSKSVDGIIDSGDDLHMGTQKFKAVIDGNGFKGT

WTENGGGDVSGRFYGPAGEEVAGKYSYRPTDAEKGGFGVFAGKKEQD;

The protein disclosed in FIG. 4 or FIG. 13 of WO97/28273;

A protein comprising an amino acid sequence selected from the group consisting of SEQ IDs 1-8 disclosed in WO96/29412 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs);

A protein comprising an amino acid sequence selected from the group consisting of SEQ IDs 1-23 disclosed in WO95/03413 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs);

A protein comprising an amino acid sequence consisting of SEQ ID 2 disclosed in WO99/31132 (or a protein comprising an immunogenic fragment of SEQ ID 2, or a protein comprising a sequence having sequence identity (preferably greater than 50% eg. 60%, 70%, 80%, 90%, 95%, 99% or more) to SEQ ID 2);

A polysaccharide antigen against *Neisseria meningitidis* serogroup A;

A polysaccharide antigen against *Neisseria meningitidis* serogroup Y;

A polysaccharide antigen against *Neisseria meningitidis* serogroup W;

A polysaccharide antigen against *Haemophilus influenzae*;

A polysaccharide antigen against *pneumococcus*;

A protective antigen against diphtheria, consisting of a diphtheria toxoid, such as the CRM197 mutant [eg. Del Guidice et al. (1998) *Molecular Aspects of Medicine* 19:1-70].

A protective antigen against tetanus, consisting of a tetanus toxoid [eg. Wassilak & Orenstein, Chapter 4 of *Vaccines* (eds. Plotkin & Mortimer), 1988]

A protective antigen against whooping cough, comprising pertussis holotoxin (PT) and filamentous haemagglutinin (FHA); optionally further comprising pertactin and/or agglutinogens 2 and 3 [eg. Gustafsson et al. (1996) *N. Engl. J. Med.* 334:349-355; Rappuoli et al. (1991) *TIBTECH* 9:232-238].

A protective antigen against *H. pylori*, comprising one or more of CagA (eg. WO93/18150), VacA (eg. WO93/18150), NAP (eg. WO99/53310), HopX (eg. WO98/04702), HopY (eg. WO98/04702), urease.

A protective antigen against hepatitis B virus, consisting of a HBV surface antigen and/or a HBV core antigen.

Where component (c) comprises an antigen against diphtheria, it preferably also comprises antigens against tetanus and polio. Where component (c) comprises an antigen against tetanus, it preferably also comprises antigens against diphtheria and polio. Where component (c) comprises an antigen against polio, it preferably also comprises antigens against diphtheria and tetanus.

Pertussis toxin is a toxic protein and, when present in component (c), it is preferably detoxified. Detoxification may be by chemical and/or genetic means. A preferred detoxified mutant is the 9K/129G double mutant [eg. Rappuoli (1997) *Nature Medicine* 3:374-376].

Where component (c) includes a protein that exists in different nascent and mature forms, the mature form of the protein is preferably used. For example, where NspA is included, (WO96/29412; see also Martin et al. (1997) *J. Exp. Med* 185 1173-1183) the mature form of the protein lacking the signal peptide is preferably used.

Where component (c) includes a polysaccharide antigen, the polysaccharide is preferably conjugated to a carrier protein.

Component (c) preferably should not diminish the immune responses raised in response to components (a) and (b).

Pharmaceutically Acceptable Carrier

The compositions of the invention may also comprise a pharmaceutically acceptable carrier.

The carrier can be organic, inorganic, or both. Suitable carriers well known to those of skill in the art and include, without limitation, large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991). Pharmaceutically acceptable carriers in compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

The carrier can also function as an immunostimulatory agent e.g. an adjuvant. Suitable adjuvants are well known to those of skill in the art.

Preferred carriers are aluminum hydroxide (alum) and MF59™.

Alum can be obtained from Superfos, Bedbaek, Denmark, and is a 3% solution. When present, ~1 mg to ~1.67 mg of alum is used per dose.

Where component (c) includes a hepatitis B antigen, aluminium hydroxide is preferably not used as a carrier (e.g. EP-A-0642355). Similarly, where component (c) includes a *H. influenzae* polysaccharide conjugate, aluminium hydroxide is preferably not used as a carrier (e.g. EP-A-0833662). Aluminium phosphate may be used instead.

MF59™ is a micro-fluidized emulsion of squalene in water that has been shown to be safe and to augment serum antibody responses to a variety of vaccines. MF59™ comprises about 5% squalene, 0.5% TWEEN 80™ and about 0.5% SPAN 85™. The adjuvant MF59™ is described in WO 90/14837. MF59™ can be made according to the procedures described in, for example, Ott et al. in *Vaccine Design: The Subunit And Adjuvant Approach* (1995, Powell and Newman, Eds., Plenum Press, New York, p. 277-296); Singh et al. (1998) *Vaccine* 16, 1822-1827; Ott et al. (1995) *Vaccine* 13, 1557-1562; Valensi et al. (1994) *J. Immunol.* 153, 4029-39.

Other carrier-adjuvants that may be used include oil-in-water emulsion formulations (with or without other specific immunostimulating agents such as muramyl peptides or bacterial cell wall components), such as for example (a) MF59™ as described above (optionally containing various amounts of MTP-PE although not required) (b) SAF, containing 10% Squalane, 0.4% TWEEN 80™, 5% PLURONIC L121™, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN 80™ Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc; and (6) other substances that act as immunostimulating agents to enhance the effectiveness of the composition.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

Immunogenicity

As used herein, the term "immunogenic" refers to material which induces the production of antibody upon administration to a vertebrate, including humans.

The compositions of the invention will typically employ an immunologically effective amount of components (a), (b) and (c). That is, there will be included an amount of component (a), (b) or (c) which, in combination with any adjuvant present, will cause the subject to produce a specific and sufficient immunological response, preferably a T or B lymphocyte response, so as to impart protection to the subject from subsequent exposure to Neisseria.

An "immunologically effective amount," is effective, either in a single dose or as part of a series, for inducing the production of antibody for either the treatment or prevention of disease. This amount will vary depending upon a variety of factors, including the physical condition of the subject, and can be readily determined by someone of skill in the art.

No single dose designation can be assigned which will provide specific guidance for each and every antigen which can be employed in this invention. The effective amount of antigen will be a function of its inherent activity and purity and is empirically determined by those of ordinary skill in the art via routine experimentation.

The immunogenic compositions according to the present invention will typically comprise an immunostimulatory amount of Neisseria antigen. An immunostimulatory amount is that amount which is sufficient to induce a measurable humoral or cellular immune response. For example, the immunogenic compositions of the present invention comprise about 1 nanogram to about 1000 micrograms of antigen or about 10 nanograms to about 800 micrograms of antigen. In some preferred embodiments, the immunogenic compositions contain about 0.1 to about 500 micrograms of antigen. In some preferred embodiments, the immunogenic compositions contain about 1 to about 350 micrograms of antigen. In some preferred embodiments, the immunogenic compositions contain about 25 to about 250 micrograms of antigen. In some preferred embodiments, the immunogenic compositions contain about 100 micrograms of antigen. One skilled in the art can readily formulate an immunogenic composition comprising any desired amount of antigen, which can be empirically determined by those of ordinary skill in the art via routine experimentation. The immunogenic compositions can be conveniently administered in unit dosage form and can be prepared by any of the methods well known in the pharmaceutical art, for example, as described in Remington's Pharmaceutical Sciences (Mack Pub. Co., Easton, Pa., 1980)

Vaccines

The present invention is also directed to vaccines comprising any of the immunogenic compositions described above.

As used herein, the term "vaccine" means an immunogenic composition which is able to induce a microbicidal immune response. Preferably, the vaccines of the present invention elicit a bactericidal antibody response.

Vaccines according to the invention may either be prophylactic (ie. to prevent infection) or therapeutic (ie. to treat disease after infection).

The invention also provides a method of inducing an immune response at least to NmB and NmC, or vaccinating, comprising administering an immunologically effective amount of an immunogenic composition of the invention. Administration can be to a human, and may be by any mode known to those skilled in the art, including by parenteral, rectal, intraperitoneal, intramuscular, of subcutaneous routes. Direct delivery will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. WO98/20734), needles, and gene guns or hyposprays. Dosage treatment may be a single dose schedule or a multiple dose schedule.

The invention also provides the compositions of the invention for use as medicaments. It further provides the use of a composition of the invention in the manufacture of a medicament for treating or preventing infection due to Neisserial bacteria.

As an alternative to protein-based vaccines, nucleic acid vaccination may be employed [eg. Robinson & Torres (1997) Seminars in Immunology 9:271-283; Donnelly et al. (1997) Annu Rev Immunol 15:617-648]. One or more protein components of the compositions of the invention may thus be replaced by nucleic acid (preferably DNA) that encodes the protein.

Manufacturing Process

The invention provides a process for the manufacture of a composition according to the invention, comprising mixing components (a), (b) and (c).

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Definitions

Standard abbreviations for nucleotides and amino acids are used in this specification.

The term "comprising" means "including" as well as "consisting" eg. a composition "comprising" X may consist exclusively of X or may include something additional to X, such as X+Y.

Identity between proteins is preferably determined by the Smith-Waterman homology search algorithm as implemented in the MPSRCH program (Oxford Molecular), using an affine gap search with parameters gap open penalty=12 and gap extension penalty=1.

BRIEF DESCRIPTION OF DRAWINGS

In all figures, Group A is data at 28 days post 1, and Group B is data at 18 days post 2.

MODES FOR CARRYING OUT THE INVENTION

The invention is further illustrated by way of the following examples which are intended to elucidate the invention. The foregoing examples are meant to illustrate the invention and are not to be construed to limit the invention in any way. Those skilled in the art will recognise modifications that are within the spirit and scope of the invention.

Example 1

ELISA Results

Groups of guinea pigs (n=15 animals) received one of the vaccines set forth in Table 1:

TABLE 1

| Group | Components | Amount per dose |
|---|---|---|
| Group 1 | NmC conj./alum | 10 µg/1 mg |
| Group 2 | NmB/alum | 25 µg/1 mg |
| Group 3 | NmC polysaccharide/NmB/alum | 10 µg/25 µg/1 mg |
| Group 4 | NmC conj./NmB/alum | 10 µg/25 µg/1 mg |
| Group 5 | NmC conj./NmB/MF59 ™ | 10 µg/25 µg/0.5 ml. |
| Group 6 (n = 5) comprised control animals that received alum alone. | | |

Eighty guinea pigs were randomised into the groups set forth above and received one of six vaccine combinations. For the data presented in Table 2, each animal received two injections, IM, separated by 28 days. Serum samples were obtained prior to each injection, and 18 days after the second injection. For the data presented in FIGS. 1A and 1B, each animal received 20 two immunisations separated by six weeks. Each dose consisted of two 0.25 ml IM injections. Serum samples were obtained immediately prior to each injection, and 14 or 18 days after the second injection.

Figure 1A:
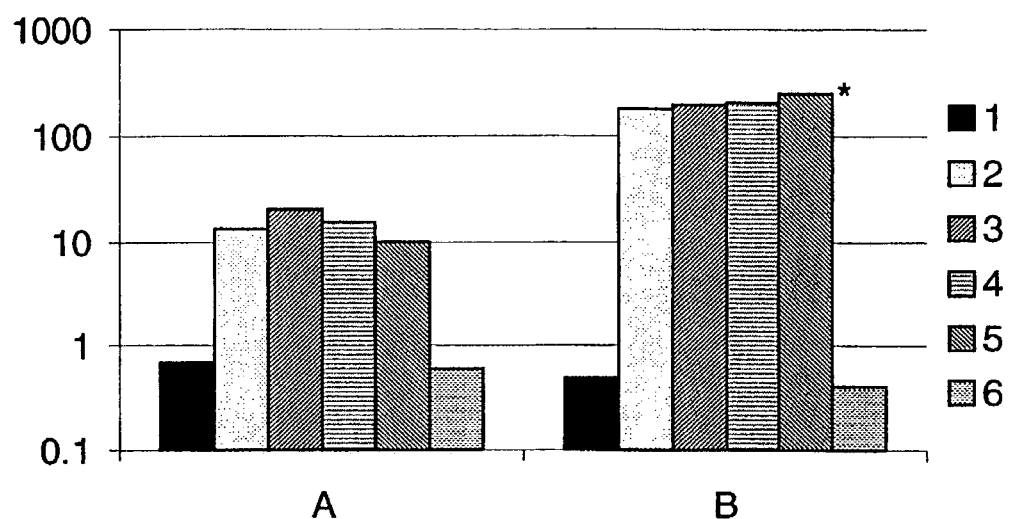
FIGS. 1A and 1B show the geometric mean IgG antibody titres (KU/nil) against (1A) NmB OMV and (1B) NmC capsule, as determined by ELISA. The * indicates (1A) $P<0.03$ for group 5 vs. groups 2 & 3, (1B) $P<0.02$ for group 5 vs. groups 1 & 4.
Figure 1B:
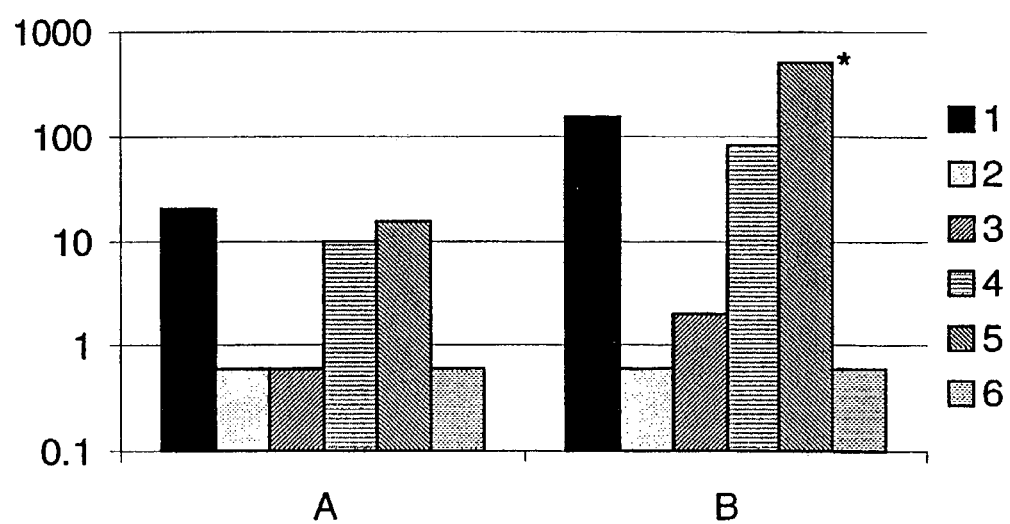

Serum samples were assayed for IgG anticapsular antibody concentrations to NmC (Table 2 and FIG. 1A) and for IgG anti-outer membrane vesicle (OMV) antibody concentrations to NmB by ELISA (FIG. 1B). The ELISA data were generated in a representative assay of individual animal sera (Table 2) and also expressed as averages from a plurality of assays (FIGS. 1A & 1B). The summary ELISA data in Table 2 are, therefore, expressed as geometric means.

For the ELISA, MCPS-ADH (NmC polysaccharide-adipic acid dihydrazide) conjugate or OMV components was coated onto polystyrene microtiter plates overnight at 4° C., 1 µg/ml, 100 µl/well. On each coated plate, 100 µl/well of each of a reference standard (i.e., pooled guinea pig serum), a positive control, a negative control, and the serum samples were two-fold serially diluted in a buffer containing 75 µM ammonium thiocyanate, and incubated for two hours at room temperature. Rabbit anti-guinea pig IgG antibody conjugated to peroxidase was added to the wells (100 µl/well). After 2 hours; the colorimetric substrate 3,3',5,5', Tetramethylbenzidine (TMB) (100 µl/well) was added, and the color was developed for 15 minutes. The levels of antibodies to MCPS and to OMV present in the controls and samples were obtained from a standard curve using the reference standard which has an assigned value of 100 ELISA units/ml. The results are shown in Table 2 and FIGS. 1A and 1B.

The results summarised in Table 2 and FIGS. 1A and 1B reveal that the combination vaccine was immunogenic, as measured by NmB and NmC IgG antibody titers, respectively.

TABLE 2

| IgG NmC Antibody Responses (GMT) | | | |
|---|---|---|---|
| | | SCN Assay | |
| Vaccine | Adjuvant | Post-1 | Post-2 |
| NmC Conj. | Alum | 20.3 | 155 |
| MenB | Alum | <1 | <1 |
| NmC Ps + MenB | Alum | <1 | 1.5 |
| NmC Conj. + MenB | Alum | 9.5 | 71 |
| NmC Conj. + MenB | MF59 ™ | 15.2 | 426 |
| None | Alum | <1 | <1 |

FIG. 1A shows that a specific anti-meningococcal B antibody response was induced by the vaccine combinations comprising NmB. FIG. 1B shows that a specific anti-meningococcal C antibody response was induced by the vaccine combinations comprising NmC. In particular, the antibody response induced by the combination of the NmC conjugate and NmB in the presence of MF59™ adjuvant (Group 5) was significantly greater than the antibody response induced by either the NmC conjugate alone (Group 1) or the combination of the NmC conjugate and NmB in the presence of alum (Group 4). When the adjuvant MF59™ was present, the antibody titre for the combination vaccine increased approximately six-fold.

Example 2

Bactericidal Titres

Serum samples were tested for complement-mediated bactericidal titres to MenC strain 60E and MenB strain 44/76. Bactericidal titres were assayed on pooled sera from each group. Bactericidal data were generated using human complement.

Figure 2A:
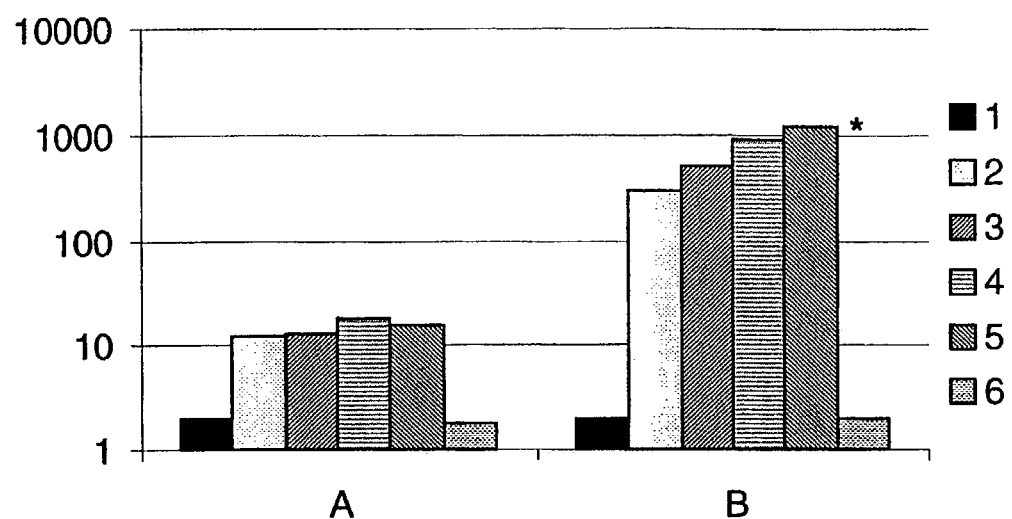
FIGS. 2A and 2B show the titres of serum bactericidal antibody (1/geometric mean titre) to (2A) NmB and (2B) NmC. The * indicates $P<0.003$ for group 5 vs. group 2.
Figure 2B:
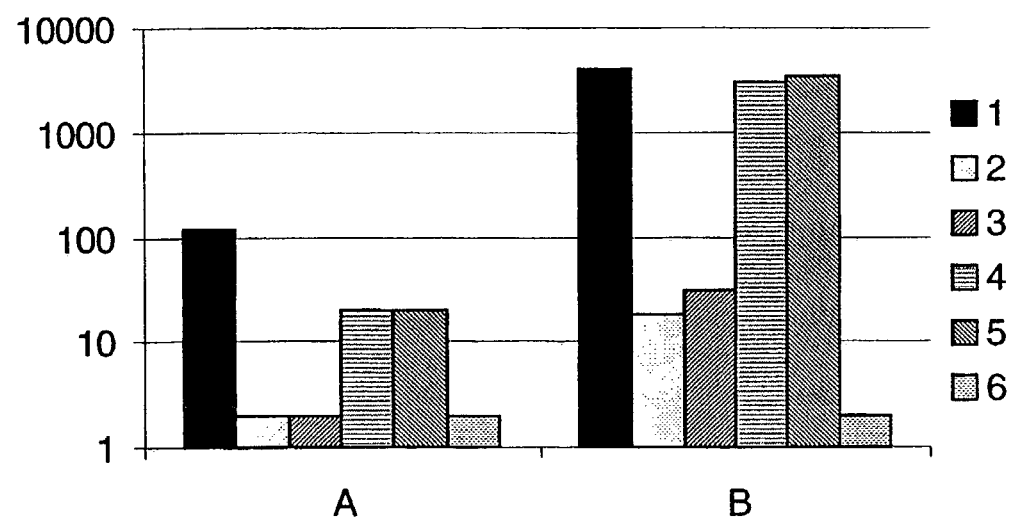

Components of the assay (i.e. buffer, antibody, complement, and bacteria) were added to sterile, 96-well tissue culture plates with lids (Nunc #167008). The plates were maintained at room temperature during the assay. To each well, 50 µl Gey's buffer (Gibco) containing 1% RIA Grade BSA (Sigma), 25 µl of the diluted test antibody, 25 µl of bacteria diluted 1:8000 in Gey's buffer/1% BSA, were sequentially added. Control wells include 1) Gey's buffer/1% BSA and bacteria alone (to determine if the organisms are viable in the diluent alone); 2) a time 0 control containing 75 µl buffer, 25 µl heat-inactivated (56° C., 30 min.) human complement, and 25 µl bacteria; and 3) a toxicity control testing the complement at 20% and 40% with buffer and bacteria to verify that the complement source is non-toxic to the test strain. All antibody samples (at the highest concentration assayed) were also tested with heat-inactivated complement to show that a decrease in colony forming units (cfu) in the presence of antibody is complement dependent. After all reagents were added, 22 µl was taken from each control well and plated onto Mueller-Hinton agar plates by allowing the sample to run from the top to the bottom of the plate, to determine the cfu in the well at 0 min. The microtitre plates were then covered and sealed with parafilm, and rotated gently for 1 hour at 37° C. in a 4% $CO_2$ incubator. The plates were then removed, and a 22 µl sample from each well plated on Mueller-Hinton agar. The culture plates were incubated for about 18 hours at 37° C., with 4% $CO_2$. The colonies were counted, and % survival determined for each test well: % survival=([cfu of sample well at 60 min]/[cfu in the heat inactivated complement control well at time 0 miin.])×100. Bactericidal titres reported are those which resulted in 50% survival. Results from a single experiment are presented in Table 3. Results are also presented in FIGS. 2A and 2B, with FIG. 2B representing average titres from a plurality of experiments.

As the results summarized in Table 3 reveal, the combination vaccine elicited high titers of serum bactericidal antibody for both NmB and NmC. Bactericidal NmC antibody titer was slightly higher for the combination vaccine using MF59™ as the carrier, but there was essentially no effect on bactericidal NmB titer using MF59™. Interestingly, two-to five-fold higher NmB bactericidal titers were obtained with the combination vaccine than with the NmB vaccine alone. FIG. 2A demonstrates that the antibodies directed to meningococcal B induced by the vaccine combinations comprising NmB were bactericidal. FIG. 2B demonstrates that the antibodies directed to meningococcal C induced by the vaccine combinations comprising NmC conjugate were also bactericidal.

TABLE 3

| Group Vaccine | NmC (1/titer) | | | NmB (1/titer) | | |
|---|---|---|---|---|---|---|
| | Pre | Post-1 | Post-2 | Pre | Post-1 | Post-2 |
| NmC conj. + Alum | <5 | 80 | >3375 | <5 | <5 | <5 |
| NmB + Alum | <5 | <5 | 15 | <5 | 15 | 800 |
| NmC Ps + NmB + Alum | <5 | <5 | 30 | <5 | 25 | 1500 |
| NmC Conj. + NmB + Alum | <5 | 25 | 2000 | <5 | 25 | 5000 |
| NmC Conj. + NmB + MF59 ™ | <5 | 50 | >3375 | <5 | 25 | 4000 |
| Alum | <5 | <5 | <5 | <5 | <5 | <5 |

Example 3

Comparison of Alum and MF59™ Adjuvants

Serum from the animals described above in FIGS. 1A and 1B were compared and MenC and MenB antibody responses generated by NmB/NmC conj. in either alum or MF59™ adjuvant were detected as described above in Examples 1 and 2. The results are shown in Table 4:

TABLE 4

Ratios of antibody responses of animals given combination of NmB OMVs + NmC conjugate, with either Al(OH)$_3$ or MF59 ™ adjuvant

| Assay | Ratio of GMT MF59 ™:GMT Al(OH)$_3$ | |
|---|---|---|
| | 28 days, post-1 | 18 days, post-2 |
| NmC | | |
| IgG | 1.6 | 6.0** |
| Bactericidal | 1.0 | 1.2* |
| NmB | | |
| IgG | 0.7 | 1.4 |
| Bactericidal | 0.9 | 1.4 |

*pooled sera only tested
**p ≤ 0.001

These data demonstrate that the antibody response to meningococcus C was approximately 6-fold greater in vaccines comprising MF59™ adjuvant.

Example 4

Comparison of Responses Generated by Combination vs. Monovalent Vaccines

Serum from the animals described above in FIGS. 1A and 1B were compared and MenC and MenB antibody responses generated by NmB/NmC conj. were compared with the antibody responses generated by either the NmB vaccine alone or the NmC conj. alone in alum as described above in Examples 1 and 2. The results are shown in Table 5:

TABLE 5

Ratios of antibody responses of animals given combination/Al(OH)$_3$ vs. monovalent/Al(OH)$_3$

| Assay | Ratio of GMT combo:GMT mono | |
|---|---|---|
| | 28 days, post-1 | 18 days, post-2 |
| NmC | | |
| IgG | 0.5 | 0.5 |
| Bactericidal | 0.2* | 0.7* |
| NmB | | |
| IgG | 1.3 | 1.2 |
| Bactericidal | 1.6 | 2.9** |

*pooled sera only tested
**p ≤ 0.05

These data demonstrate that there is no significant difference in the antibody responses to the components of the NmB/NmC conj. vaccine compared to the responses induced by the respective monovalent vaccines (either NmB or NmC conj.).

Example 5

Addition of Further Antigens

The NmB/NmC combination is further augmented by adding antigens against other pathogenic organisms (e.g. NspA, HBsAg). Good immune responses are observed against NmB/NmC and against the additional antigens.

Example 6

Mixtures of NmB and NmC Antigens

A trivalent mixture of strain 2996 MenB proteins '919' (e.g. WO99/57280 FIG. 23 and SEQ IDs 3069-3074 therein), '287' (e.g. FIG. 21 of WO99/57280; also SEQ IDs 3103-3108 therein) and 'ORF1' (e.g. example 77 of WO99/24578; see also WO99/55873) was used to immunise mice. The experiment was repeated with the addition of NmC conjugate. Aluminium hydroxide was used as adjuvant.

Titres measured in a bactericidal assay against the homologous strain and also heterologous MenB strains were as follows:

| | 2996 | BZ133 | BZ232 | 1000 | MC58 | NGH38 |
|---|---|---|---|---|---|---|
| Trivalent | 2048 | 2048 | 4 | <4 | 64 | 4 |
| +NmC | 2048 | >32000 | 4 | 128 | 1024 | 128 |

It will be understood that this application describes the invention by way of example only and modifications may be made whilst remaining within the scope and spirit of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09636393B2). An electronic copy of the "Sequence Listing" will also be available from the USPTO upon request and payment of the fee set forth in 37 CFR 1.19(b)(3).

The invention claimed is:

1. A composition comprising (a) *Neisseria meningitidis* C (NmC) oligosaccharide conjugated to a carrier protein, (b) *Neisseria meningitidis* B (NmB) outer membrane protein, and (c) an isolated polypeptide comprising an amino acid sequence having 80% or greater sequence identity to SEQ ID NO: 601, wherein the components (a), (b) and (c) were mixed together and wherein the composition comprises a carrier-adjuvant selected from aluminum hydroxide, aluminum phosphate, and an oil-in-water emulsion.

2. The composition of claim 1 further comprising (d) a protective saccharide antigen against *Neisseria meningitidis* serogroup A.

3. The composition of claim 1 further comprising (d) a protective saccharide antigen against *Neisseria meningitidis* serogroup W.

4. The composition of claim 1 further comprising (d) a protective saccharide antigen against *Neisseria meningitidis* serogroup Y.

5. The composition according to claim 1, wherein the NmB outer membrane protein is present as proteoliposomic vesicles.

6. The composition of claim 1, wherein the carrier protein is CRM197.

7. A composition comprising (a) *Neisseria meningitidis* C (NmC) oligosaccharide conjugated to a carrier protein, (b) *Neisseria meningitidis* B (NmB) outer membrane protein, and (c) a polypeptide comprising an amino acid sequence having 80% or greater sequence identity to SEQ ID NO: 601, wherein the components (a), (b) and (c) were mixed together and the carrier protein is a non-toxic diphtheria toxin.

* * * * *